United States Patent [19]

Trick

[11] Patent Number: 4,549,531
[45] Date of Patent: Oct. 29, 1985

[54] ARTIFICIAL SPHINCTER WITH INFLATABLE CUFF

[75] Inventor: Robert E. Trick, Racine, Wis.

[73] Assignee: Medical Engineering Corporation, Racine, Wis.

[21] Appl. No.: 637,335

[22] Filed: Aug. 3, 1984

Related U.S. Application Data

[63] Continuation of Ser. No. 371,529, Apr. 26, 1982, abandoned.

[51] Int. Cl.⁴ .......................... A61B 19/00; A61F 1/00
[52] U.S. Cl. .............................. 128/1 R; 128/DIG. 25; 128/346; 623/14
[58] Field of Search ................ 128/92, 1 R, 327, 346; 24/201; 3/1

[56] References Cited

U.S. PATENT DOCUMENTS

| | | | |
|---|---|---|---|
| 2,455,859 | 12/1948 | Foley | 128/327 |
| 3,538,917 | 11/1970 | Selker | 128/326 |
| 3,654,931 | 4/1972 | Hazlewood | 128/327 |
| 3,730,186 | 5/1973 | Edmunds et al. | 128/325 |
| 3,789,828 | 2/1974 | Schulte | 128/325 |
| 3,863,622 | 2/1975 | Buuck | 128/1 R |
| 4,161,806 | 7/1979 | Hennisse et al. | 24/201 |
| 4,175,562 | 11/1979 | Honan | 128/327 |
| 4,222,377 | 9/1980 | Burton | 128/1 R |
| 4,408,597 | 11/1983 | Tenney, Jr. | 128/346 |

Primary Examiner—Richard J. Apley
Assistant Examiner—David J. Isabella
Attorney, Agent, or Firm—Quarles & Brady

[57] ABSTRACT

The inflatable cuff of an artificial sphincter is secured in place about a natural body passage by fastening means which consist of a reinforcing belt for encircling the cuff and a clip to hold the belt in place. The belt has a reinforcing intermediate section of substantially uniform thickness throughout and a pair of ends, each of which have enlarged beads at their tips. At least one of the ends of the belt has a pair of spaced apart fingers which are especially useful for extending through the mesentery without interfering with the blood supply of said passage and the clip has bead receiving and retaining cavities for securing the belt in place.

1 Claim, 7 Drawing Figures

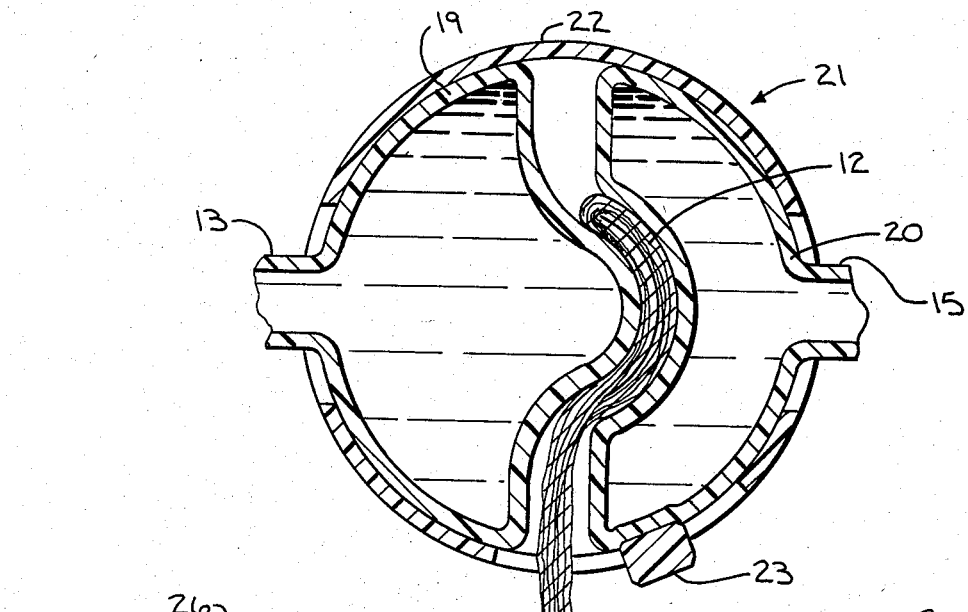
FIG.3
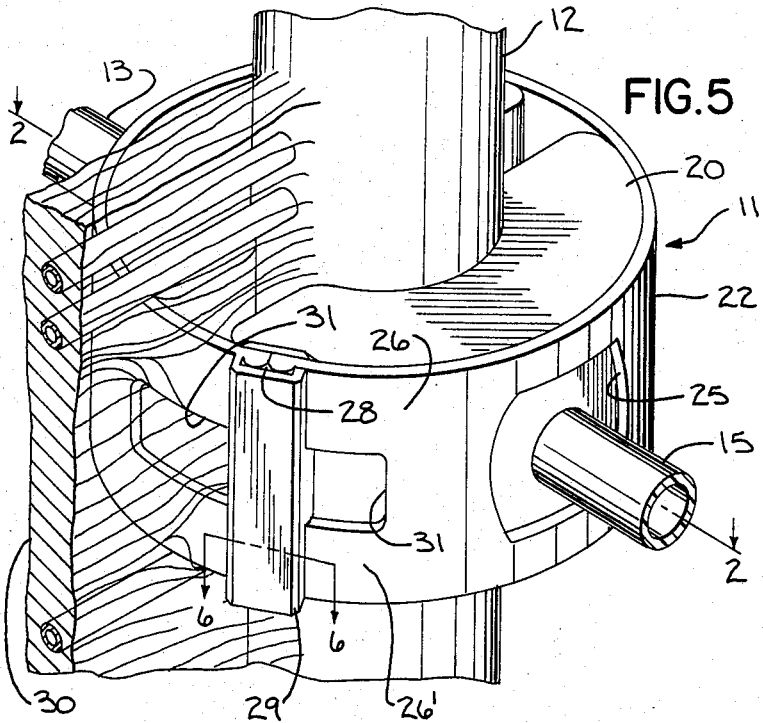
FIG.4
FIG.5
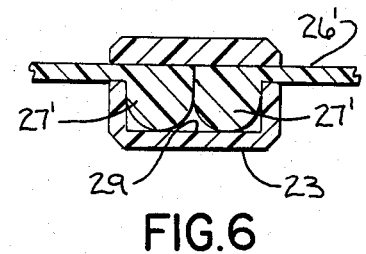
FIG.6

ARTIFICIAL SPHINCTER WITH INFLATABLE CUFF

RELATED APPLICATION

This application is a continuation of application Ser. No. 371,529, filed Apr. 26, 1982, now abandoned.

FIELD OF THE INVENTION

This invention relates generally to an artificial sphincter for removably closing a body passageway, and more particularly to an artificial sphincter with an inflatable cuff and improved means for securing the cuff in place about a natural body passage, such as the urethra or colon, without interfering with the vascularization of the passage.

BACKGROUND OF THE INVENTION

Many people have nonfunctioning or malfunctioning natural sphincters which make it impossible for them to control the discharge of body wastes through body passages.

One of the most common troublesome and embarrassing such conditions is the malfunctioning of the urethral sphincter. Normally, the urethral sphincter is responsible for controlling the flow of urine from the bladder of a person. When the urethral sphincter is malfunctioning the flow of urine from the bladder cannot be controlled. Obviously, this can be embarrassing to an individual and restrict his activities. A similar problem exists where the rectal sphincter fails to function properly.

A number of attempts have been made in the past to provide artificial sphincters which can substitute for a malfunctioning natural sphincter, or to control an artificially created body passage which has no natural sphincter.

The earliest artifical sphincters were external devices. However, in recent years, artificial sphincters have been developed which are implanted within the abdominal cavity of the patient. One example of such an implantable aritifical sphincter is that disclosed in the Reinicke U.S. Pat. No. 4,167,952. The sphincter disclosed in the Reinicke patent is a hydraulic system which includes a normally inflated cuff for encircling the urethra, a control unit including a reservoir for inflating fluid and a valve for controlling the fluid pressure in the cuff to minimize tissue damage and tubing connecting the control unit to the cuff. The valve of the control unit can be manually opened by digital pressure to deflate the cuff and open the urethra. The cuff can be reinflated to close the urethra by exerting digital pressure on the reservoir of the control unit.

Recently, an implantable aritifical sphincter system has been proposed which has a double chambered cuff in which one chamber of the cuff is maintained at a relatively constant static pressure and the other chamber of the cuff is inflated to collapse the vessel against the first chamber and deflated to permit the vessel to open. The chamber of the cuff which is maintained at a static pressure does not have to be inflated or deflated once its internal pressure has been established at the proper level. The other chamber of the cuff, which can be inflated and deflated, is a part of a hydraulic system, like that of Reinicke.

Implantable, artificial sphincters which have either a single chamber cuff such as that disclosed in the Reinicke patent or the recently proposed double chamber cuff require that the cuff be securely positioned about the vessel to be controlled. Generally, this has been done by tying or suturing the cuff in place. In addition to being time consuming, in some instances, securing the cuff in place in such a manner has interfered with the blood supply for the tissue of the wall passage, such as the colon, which is furnished by blood vessels in the mesentery connecting the body passage to the peritoneum. This has resulted in tissue necrosis requiring the removal or replacement of the artificial sphincter.

SUMMARY OF THE INVENTION

It is an object of the present invention to provide an improved means for securing an inflatable cuff of an implantable artificial sphincter in place about a natural body vessel, such as the urethra.

It is a further object of the invention to disclose a simple, easy to use means for securing either a one chamber or a two chamber inflatable cuff of an artificial sphincter in place without the need for tying or suturing.

The present invention relates to a simple, reliable, improved means for securing a cuff of an implantable artificial sphincter in place about a natural passage, such as a urethra, without interfering with the vascularization of the tissue of the wall of the passage which can result in necrosis requiring the removal or replacement of the artificial sphincter.

Briefly, the present invention relates to means for securing an inflatable cuff of an implantable artificial sphincter in place which means comprise an elongated, reinforcing belt for encircling the cuff and securing it in place about the body vessel and a clip for securing the ends of the belt together once it is in place.

The preferred belt has a cuff encircling and reinforcing intermediate section of substantial uniform thickness and each of the two ends of the belt has a pair of flexible fingers designed to extend through the mesentery without interfering with the vessels which supply blood to the tissue of the vessel wall. The ends of each of the fingers has an enlarged bead and the clip for securing the ends of the belt together has cavities for receiving and retaining beads on the finger tips.

The novel fastening means of the present invention will now be described in conjunction with the drawings.

BRIEF DESCRIPTION OF THE DRAWINGS

In the drawings:

FIG. 3 is a view similar to that of FIG. 2 with the cuff inflated and the passage closed;

FIG. 4 is a perspective view of the preferred belt of the fastening means;

FIG. 5 is a schematic view showing the fastening means of the present invention securing a double chambered inflatable cuff in position about a body passage in which blood is supplied to the body passage tissue by vessels in the mesentery;

FIG. 6 is a view taken along the line 6—6 in FIG. 5; and

DESCRIPTION OF THE PREFERRED EMBODIMENT

Figure 1:
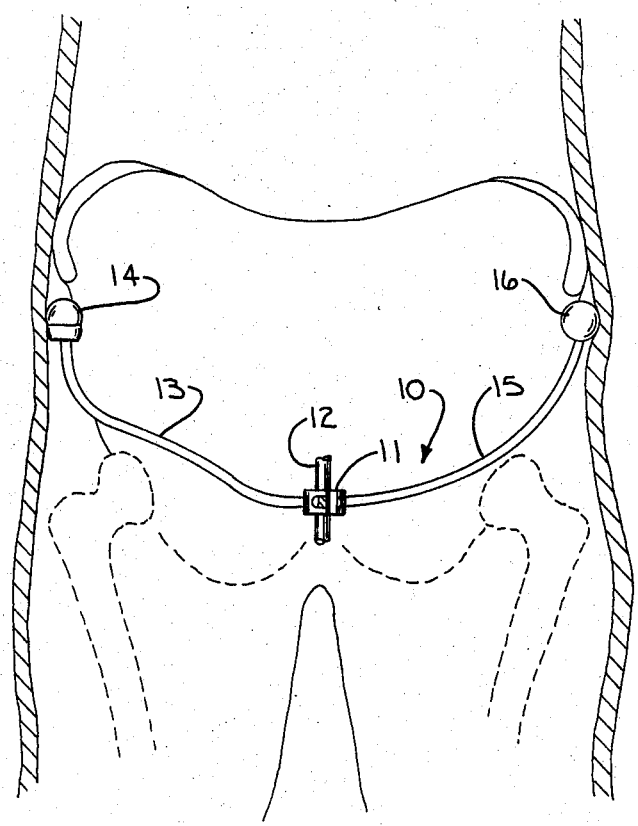
FIG. 1 is a front sectional view depicting the trunk of a human body having an artificial sphincter system implanted therein with a cuff secured in an encircling relationship about a section of the urethra by the fastening means of the present invention.

In FIG. 1 can be seen an artifical sphincter system generally designated as 10, which includes a cuff 11 operatively positioned about a body passage 12, the urethra, in the abdominal cavity of a human. Tubing 13 leads from one side of the cuff 11 to a control unit 14 and tubing 15 leads from the other side of the cuff 11 to a resealable septem 16.

Figure 2:
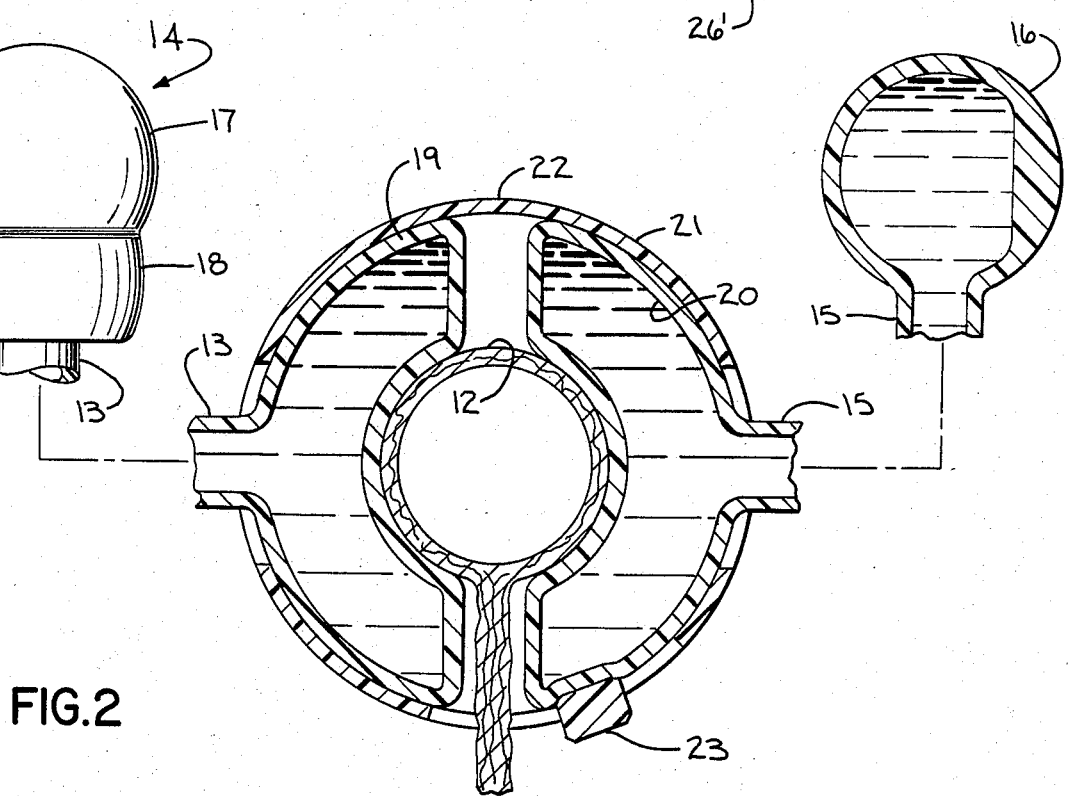
FIG. 2 is a schematic view showing a cuff of an artificial sphincter secured in position about an open body passage by the fastening means of the present invention.

The control unit 14 is preferably a manually operable unit, such as that disclosed in the Reinicke U.S. Pat. No. 4,167,952 issued Sept. 18, 1979, which is incorporated by reference herein. As seen in FIG. 2, the Reinicke control unit includes a deformable elastic bulb reservoir 17 which contains inflating fluid and a manually operable valve 18. The bulb reservoir 15 is squeezed to inflate the cuff 11 to close the body passage 12 as seen in FIG. 3 and the valve 18 is manually operated to deflate the cuff 11 and open the body passage 12 as seen in FIG. 2. The cuff 11 is normally inflated closing the body passage 12 as seen in FIG. 3.

As seen in FIGS. 2, 3 and 5, the cuff 11 is actually made up of two separate and distinct cuff chambers 19 and 20 which are held in place about the body passage 12 by fastening means, generally designated as 21. It is the cuff chamber 19 which is connected by the tubing 13 to the control unit 14 and the chamber 20 which is connected by the tubing 15 to the septum 16.

In the double chamber artificial sphincter system illustrated in FIGS. 1, 2, 3 and 5, the cuff chamber 20 is normally maintained at a constant static fluid pressure and the cuff chamber 19 is inflated to collapse the body passage 12 against the cuff chamber 20 as seen in FIG. 3. The cuff chamber 19 is deflated by manually squeezing the valve 18 of the control unit 14 whereupon fluid flows from the cuff chamber 19 to the deformable elastic bulb reservoir 15. The pressure in cuff chamber 20 can be adjusted by adding or removing fluid with a needle inserted through the resealable septum 16.

As seen in FIGS. 2, 3 and 5, the two chambers 19 and 20 of the cuff are secured in position encircling the body passage 12 by the fastening means 21 which includes a cuff encircling belt 22 and a clip 23 for holding the ends of the belt 22 in place.

Figure 7:
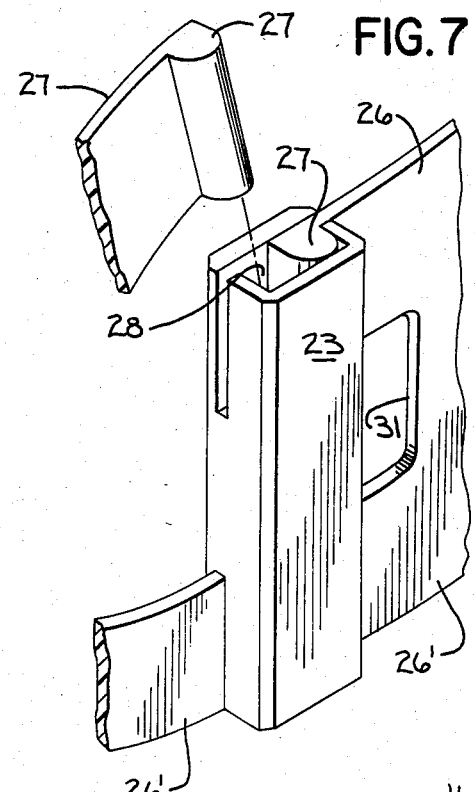
FIG. 7 is an enlarged view showing the manner in which the ends of the belt of the fastening means of the present invention are inserted in and retained by the clip.

Referring now to FIG. 4, it can be seen that the belt 22 is an enlongated member having a pair of spaced apart cuff tubing windows 24 and 25. Each end of the belt 22 has a pair of fingers 26, 26' having enlarged beads 27, 27' at their tips. The belt 22 preferably is made of silicone rubber and is mesh reinforced As seen in FIGS. 5, 6 and 7, the clip 23 has a bead receiving and retaining cavity at the top 28 and another 29 at the bottom.

FIG. 5 illustrates the use of the fastening means 21 under conditions of use on a body passage 12, such as the colon, which is supplied by blood vessels in the mesentery connecting the colon to the peritoneum. In FIG. 5 the belt 22 is positioned encircling the two cuff chambers 19 and 20 and the body passage 12 with tubing 13 and tubing 15 extending through windows 24 and 25, respectively. The beaded ends 27, 27' of each of the ends of the belt 22 are in the bead receiving and retaining cavities 28 and 29, respectively of the clips 23. The fingers 26, 26' of one end of the belt are seen extending through the mesentery 30 which supplies blood to the tissue of the wall of the colon. The space 31 between the fingers 26 and 26' of each end of the belt 22 permit the belt 22 to be positioned so that the major blood vessels in the mesentery can be avoided. As a result, there is a minimum interference with the vascularization of the tissue wall and the risk of necrosis is substantially eliminated It will be readily apparent to those skilled in the art that a number of modifications and changes can be made without departing from the spirit and scope of the present invention. For example, although in the preferred embodiment, the fastening means of the present invention is shown and described in connection with securing a double chamber cuff in place around a body passage, it also could be used to attach a different design cuff in place about any natural or artificial body passages. The belt 22 is shown in the drawings as having a pair of fingers at each end, however, there may be some applications in which it would be desirable to have additional fingers. Likewise, there may be applications in which a clip, other than that specifically shown in the drawings, might be used. Finally, although the belt has been described as being made of silicone elastomer reinforced with mesh, both the belt and the clip could be made of any other biocompatible material, if desired. In view of the foregoing and other changes, it is intended that the invention not be limited except by the claims which follow.

I claim:

1. In an artificial sphincter having an inflatable cuff for closing off a body passage and fastening means for securing the cuff in position around the outer wall of the body passage, the improved fastening means which comprises:

(a) a flexible reinforcing belt for encircling the cuff and securing said cuff in place around the outer wall of the passage, said belt having an intermediate section of substantially uniform thickness throughout, and a pair of ends, at least one of said ends having a pair of relatively narrow spaced apart terminal flexible elongated fingers which can be threaded through the mesentery of the body passage so that they do not interfere with blood flow through the vessels which supply blood to the outer wall of the passage, said fingers, and the other end of said belt having enlarged beads, and (b) a separate clip for securing the two ends of the belt together once it is in place, said clip having means for receiving and retaining the beads of the fingers and the other end of the belt.

* * * * *